United States Patent [19]

Murphy

[11] Patent Number: 4,595,765

[45] Date of Patent: Jun. 17, 1986

[54] PROCESS FOR PREPARING 5,6-DIHYDROXYINDOLE

[75] Inventor: Bryan P. Murphy, Trumbull, Conn.

[73] Assignee: Clairol Incorporated, New York, N.Y.

[21] Appl. No.: 788,510

[22] Filed: Oct. 18, 1985

Related U.S. Application Data

[63] Continuation of Ser. No. 533,171, Sep. 19, 1983, abandoned.

[51] Int. Cl.$^4$ .............................................. C07D 209/26
[52] U.S. Cl. ..................................... 548/491; 548/508
[58] Field of Search ................................ 548/491, 508

[56] References Cited

U.S. PATENT DOCUMENTS

| | | | |
|---|---|---|---|
| 2,787,551 | 4/1957 | Bell et al. ............................ | 548/511 |
| 3,194,734 | 7/1965 | Seemuller et al. ................... | 548/510 |
| 3,732,245 | 5/1973 | Batcho et al. ....................... | 548/510 |
| 4,255,333 | 3/1981 | Opgenorth et al. ................. | 548/491 |
| 4,431,820 | 2/1984 | Nierenga ............................. | 548/491 |

OTHER PUBLICATIONS

Benigni, J. D. et al., J. Heterocyclic Chem., 2, 387–392, (1965).

*Primary Examiner*—George F. Lesmes
*Assistant Examiner*—S. A. Gibson
*Attorney, Agent, or Firm*—Gabriel P. Katona

[57] ABSTRACT

5,6-Dihydroxyindole is prepared by the catalytic reductive cyclization of 4,5-dihydroxy-2,$\beta$-dinitrostyrene in a single step using hydrogen with a palladium, platinum or rhodium catalyst in a polar hydroxylic reaction system. No reaction byproducts or only a single reaction byproduct are produced. The 4,5-dihydroxy-2,$\beta$-dinitrostyrene intermediate can be prepared by the chemoselective debenzylation of 4,5-dibenzyloxy-2,$\beta$-dinitrostyrene using trifluoroacetic acid. 5,6-Dihydroxyindole is a useful component in hair dye formulations and as an intermediate in the synthesis of melanin.

8 Claims, No Drawings

PROCESS FOR PREPARING 5,6-DIHYDROXYINDOLE

This is a continuing application of application Ser. No. 533,171 filed Sept. 19, 1983, now abandoned.

BACKGROUND OF THE INVENTION

1. Field of the Invention

This invention relates to a method for preparing 5,6-dihydroxyindole. More particularly, this invention relates to a one step process for preparing 5,6-dihydroxyindole from 4,5 dihydroxy-2,β-dinitrostyrene in high yields and purity by a catalytic reductive cyclization in the presence of hydrogen and a supported palladium, platinum or rhodium catalyst. The invention also relates to the preparation of the starting 4,5-dihydroxy-2,β-dinitrostyrene reactant and the reaction intermediates therefor.

2. Discussion of the Prior Art 5,6-dihydroxyindole is a known intermediate in the preparation of melanin which is an organic pigment useful in, for example, hair dye preparations. Hair dyeing compositions and methods using 5,6-dihydroxyindole or a derivative thereof are shown, for example, in U.S. Pat. Nos. 2,934,396 and 3,194,734. The hydroxyindoles are also known as anti-oxidants, see e.g. U.S. Pat. No. 2,787,551, and as intermediates in the production of amino acids, alkaloids, tryptamines, and the like, see e.g. U.S. Pat. No. 3,732,245. For these various utilities, it is essential that the 5,6-dihydroxyindole be available in high purity and under stable conditions.

Therefore, the synthesis of indoles and hydroxyindoles has received much attention, due to their broad range of uses and biological applications. In particular, extensive studies have been made of the synthesis of 5,6-dihydroxyindole and its subsequent polymerization to melanin. See, for example, Mason, H. S., J. Biol. Chem., 1948, Vol. 172, p. 83; Bu'Lock, J. D. and Harley-Mason, J., J. Chem. Soc. 1951, p. 703 and p. 2249; Cromartie, R. I. T. and Harley-Mason, J., J. Chem. Soc. 1953, p. 200; Beer, R. J. S., et al, J. Chem. Soc. 1948, p. 2223; Clemo, G. R. and Weiss, J., J. Chem. Soc. 1945, p. 702 and p. 1795; Clemo, G. R. and Duxbury, F. K., J. Chem. Soc. 1952, p. 3464 and p. 3844; Benigni, J. D., et al, J. Heterocycl Compounds, 1965, Vol. 2, p. 387; and Young, T. E., et al, J. Org. Chem. 1980, Vol. 45, p. 2901. The chemical reductive cyclization of 5-benzyloxy-2,β-dinitrostyrene to 5-benzyloxyindole using powdered iron and organic acid is shown in Canadian Pat. No. 555,760. The reductive cyclization of ortho-nitro-β-aminostyrene to the corresponding indoles by either chemical (e.g. Fe°—CH$_3$CO$_2$H) or catalytic (e.g. H$_2$—Pd/C, organic solvent) reduction is shown in U.S. Pat. No. 3,732,245. These syntheses, however, are unattractive either because of low yields or the results are difficult to reproduce on a large scale.

The isomeric 4,5-dihydroxy-2,β-dinitrostyrenes are promising intermediates in the synthesis of 5,6-dihydroxyindole. Foe example, in the above cited article by Beer, et al, acetylation, chemical reductive cyclization (Fe°—CH$_3$CO$_2$H) and deacetylation give about 35% yield as shown in the following Scheme I.

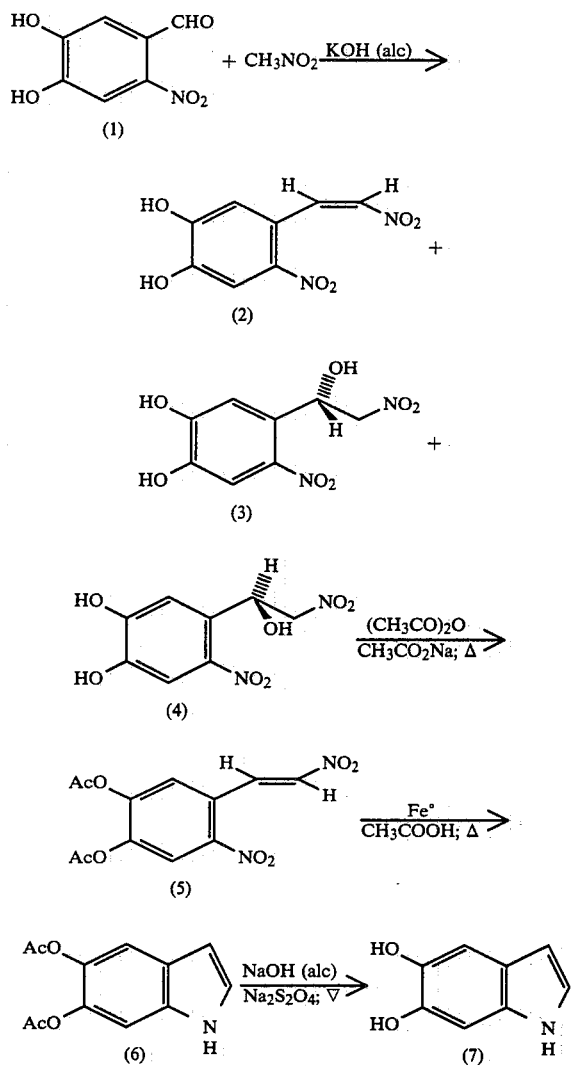

SCHEME I

However, this scheme, in addition to requiring the acetylation and deacetylation steps to protect and then unblock the hydroxyl groups also requires a complicated cyclization using elemental iron, Fe°, and acetic acid. Still further, stringent purification is required to isolate the intermediate 5,6-diacetoxyindole (6) from the resulting black gum. 5,6-Dihydroxyindole (7) resulting from the deacetylation of 5,6-diacetoxyindole is unstable under the reaction conditions (pH>7), and antioxidants (e.g. Na$_2$S$_2$O$_4$) must be included. Accordingly, the product 5,6-dihydroxyindole ideally is not used directly for the production of melanin.

Other researchers have shown the efficacy of AlX$_3$—thiol and AlCl$_3$—dichloroethane systems in the cleavage of methylenedioxy ethers. See, for example, M. Node, et al, J. Org. Chem. 1980, Vol. 45, p. 4275; and M. A. Avery, et al, J. Org. Chem., 1980, Vol. 45, p. 2750, respectively. In the latter procedure, which uses a ring opening method, 4,5-dihydroxy-2-nitrobenzaldehyde (1) is synthesized from 6-nitropiperonal (9)

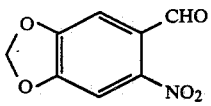

5-chloromethoxy-4-hydroxy-2-nitrobenzaldehyde (10),

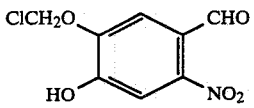

in 87.9% reported yield based on 6-nitropiperonal. Although a one-step demethylenation of 6-nitropiperonal with $AlCl_3$—$ClCH_2CH_2Cl$ seems viable, the desired product (1) is isolated in higher yield through the intermediary (10). 4,5-dihydroxy-2-nitrobenzaldehyde (1) can then be converted to 4,5-dihydroxy-2,β-dinitrostyrene (2) by known procedures, such as shown by Beer, et al. However, it has been found that the dechloromethylation of Avery, et al cannot be effectively utilized for amounts of starting material in excess of about 1 gram.

Alternate routes to (E)-4,5-dihydroxy-2,β-dinitrostyrene are also known. Thus, condensation of 3,4-dialkoxybenzaldehydes with $CH_3NO_2$, followed by nitration, gives the corresponding 4,5-dialkoxy-2, β-dinitrostyrene. However, standard ether cleavage with hydrogen halides is not useful, since hydrohalogenation occurs. It was necessary, therefore, to develop a mild method for removal of the protecting groups. Although trifluoroacetic acid ($CF_3CO_2H$) has been reported as a debenzylation reagent (March, J. P. and Goodman, L., J. Org. Chem. 1965, Vol. 30, pp. 2491-2) the authors do not elucidate on the general theory or scope of the debenzylation reaction or on its advantages. For example, it has now been found that other groups in the molecule can increase the rate of debenzylation, but these groups are not necessary for the success of the reaction. It has also now been found that $CF_3CO_2H$ is 100% selective and does not affect other functional groups in this molecule. Based on this discovery, a mild and selective method for unblocking the hydroxyl protecting benzyl grouos has now been developed using trifluoroacetic acid as the selective debenzylation agent. According to this reaction, the benzyl groups of 4,5-dibenzyloxy-2,β-dinitrostyrene are removed without reduction of the nitro groups or addition to styrene double bond as would occur with normal ether cleavage reagents (e.g. $H_2$—Pd/C, hydrogen halides, and $H_2SO_4$). Accordingly, a highly effective and novel means has been developed to prepare the 4,5-dihydroxy-2,β-dinitrostyrene compound used as the reactant for forming the object 5,6-dihydroxyindole by the selective debenzylation of 4,5-dibenzyloxy-2,β-dinitrostyrene with trifluoroacetic acid.

Previously, catalytic cyclization of 4,5-dihydroxy-2,β-dinitrostyrene (14) was unknown, although several methods are known for the corresponding dialkoxy and diaryloxy derivatives. See, for example, the above mentioned article by J. D. Benigni, et al and C. F. Heubner, et al, J. Amer. Chem. Soc. 1953, Vol. 75, pp. 5887-5890. However, these procedures which involve refluxing $CH_3CO_2H$—Fe° and 10% Pd/C—$H_2$ in organic solvents, e.g. a mixture of ethyl acetate, acetic acid, and ethanol, are not useful for cyclization of 4,5-dihydroxy-2,β-dinitrostyrene (14). Under the typical $H_2$ pressure range of from 40 to 55 pounds per square inch (psi) the cyclization of 4,5-dihydroxy-2,β-dinitrostyrene gives only a small amount of 5,6-dihydroxyindole which is contaminated with many by-products.

SUMMARY OF THE INVENTION

It is, therefore, an object of the present invention to provide a direct route for preparing 5,6-dihydroxyindole from 4,5-dihydroxy-2,β-dinitrostyrene which minimizes or totally eliminates formation of any by-products.

It is another object of this invention to provide a process for preparing 5,6-dihydroxyindole which is stable under the reaction conditions and which can be easily recovered.

A still further object of this invention is to provide a simple process for preparing 5,6-dihydroxyindole from 4,5-dibenzyloxy-2,β-dinitrostyrene by first selectively debenzylating the latter to form 4,5-dihydroxy-2,β-dinitrostyrene using trifluoroacetic acid and, thereafter, catalytically reducing the dinitrostyrene compound to 5,6-dihydroxyindole in the presence of hydrogen and a palladium, platinum or rhodium catalyst in a suitable reaction medium.

Still yet another object of this invention is to provide a more efficient process for preparing 4,5-dihydroxy-2-nitrobenzaldehyde, which can then be easily converted into 4,5-dihydroxy-2,β-dinitrostyrene, by ring-opening 6-nitropiperonal with $AlCl_3$ and dichloroethane to produce 5-chloromethoxy-4-hydroxy-2-nitrobenzaldehyde in yields in excess of 93% followed by ether cleavage to produce 4,5-dihydroxy-2-nitrobenzaldehyde.

These and other objects of the invention which will be more readily apparent from the following detailed description can be accomplished by a process for preparing 5,6-dihydroxyindole

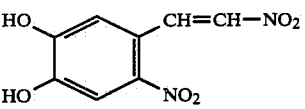

by subjecting 4,5-dihydroxy-2,β-dinitrostyrene

HO—⟨⟩—CH=CH—NO₂
HO—⟨⟩—NO₂ to catalytic reductive cyclization with hydrogen in the presence of a palladium, platinum or rhodium catalyst in a suitable reaction medium to produce the object 5,6-dihydroxyindole. According to this invention, the object 5,6-dihydroxyindole can be obtained at a yield of 95 to 100% based on the starting 4,5-dihydroxy-2,β-dinitrostyrene without any byproducts, i.e. 95 to 100% conversion at 100% selectivity. Only a single by-product is observed when a mixture of distilled water and acetic acid is used as the reaction medium.

In a further aspect of the invention, the 4,5-dihydroxy-2,β-dinitrostyrene reactant is obtained by the debenzylation of 4,5-dibenzyloxy-2,β-dinitrostyrene with trifluoroacetic acid.

In an alternative aspect of the invention, the 4,5-dihydroxy-2,β-dinitrostyrene reactant is obtained from 4,5- dihydroxy-2-nitrobenzaldehyde which in turn is prepared from 6-nitropiperonal by a two-step dimethylenation and ether cleavage reaction using aluminum trichloride and dichloroalkane solvent in the first step and hydrohalide in the second step, and then converting the resulting 4,5-dihydroxy-2-nitrobenzaldehyde into 4,5-dihydroxy-2,β-dinitrostyrene with CH₃NO₂.

DETAILED DESCRIPTION OF THE INVENTION AND PREFERRED EMBODIMENTS

In the conventional method of preparing 5,6-dihydroxyindole from 4,5-dihydroxy-2,β-dinitrostyrene three reactions are required: acetylation; chemical reductive cyclization; and deacetylation; such as shown in Scheme I, above. However, as noted by Beer, et al this method furnishes only a moderate yield of 5,6-dihydroxyindole. Moreover, 5-6-dihydroxyindole is unstable under the conditions of the chemical reduction reaction.

The present invention provides an alternative one step or direct route from 4,5-dihydroxy-2,β-dinitrostyrene to 5,6-dihydroxyindole using a catalytic reductive cyclization in a suitable reaction medium.

The overall reaction scheme starting with the commercially available 3,4-dibenzyloxybenzaldehyde (11) is shown in the following Scheme II:

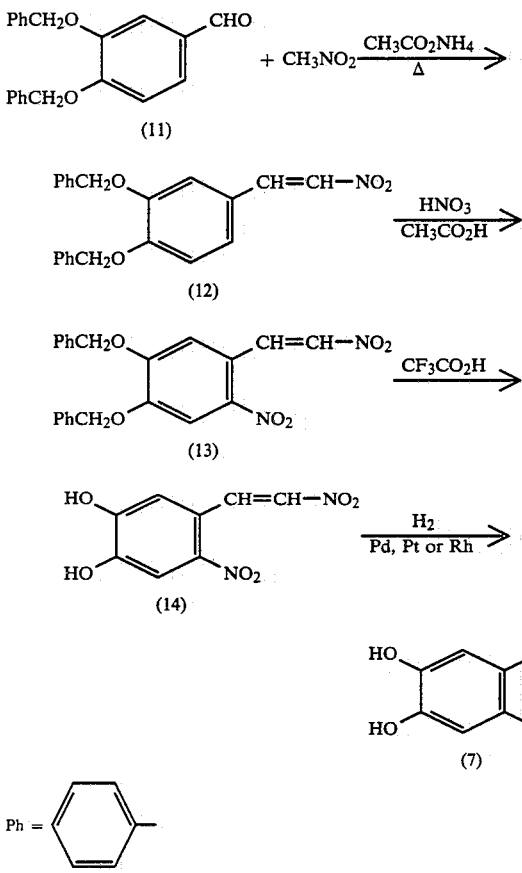

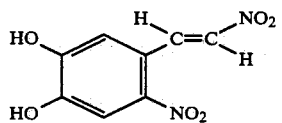

The condensation reaction of (11) to (12) with CH₃NO₂ is carried out at atmospheric pressure in a solution of CH₃CO₂NH₄ in acetic acid preferably at reflux, although the reaction will proceed at lower temperatures. 3,4-dibenzyloxy-β-nitrostyrene (12) is only slightly soluble at ambient temperature in the reaction medium and the precipitate can be recovered by filtration.

After recovery of 3,4-dibenzyloxy-β-nitrostyrene (12), this compound is nitrated according to known procedures with fuming HNO₃ to produce 4,5-dibenzyloxy-2,β-dinitrostyrene (13). The synthesis of 3,4-dibenzyloxy-β-nitrostyrene (12) and 4,5-dibenzyloxy-2,β-dinitrostyrene (13) is described in greater detail by Benigni and Minnis, J. Heterocycl. Compounds, 1965, Vol. 2, p. 387, et seq. The latter compound is then subjected to novel debenzylation reaction with refluxing trifluoroacetic acid. The debenzylation reaction preferably should be carried out in an inert nonoxidizing atmosphere, for example, in N₂ gas, argon, etc. The reaction is preferably carried out under reflux conditions and at atmospheric pressure, although the reaction will proceed at ambient temperature conditions. Since trifluoroacetic acid is liquid under the reaction conditions and is a good solvent for (13), no additional solvent or diluent is required, and preferably trifluoroacetic acid is the only reaction solvent, since it is removed easily at the end of the reaction by distillation. The amounts of 4,5-dibenzyloxy-2,β-dinitrostyrene and CF₃COOH are not particularly critical so long as sufficient CF₃COOH is present to remove both benzyl groups, and dissolve the reactants and products. Generally, therefore, at least 2, preferably from 37 to 50 equivalents of CF₃COOH are present per mole of 4,5-dibenzyloxy-2,β-dinitrostyrene, for example, a 7:1 (v/w) ratio of CF₃COOH:4,5-dibenzyloxy-2,β-dinitrostyrene. Suitable reaction times are generally in the range of from about 30 minutes to about 10 hours, preferably from about 1 hour to about 5 hours.

After the debenzylation reaction, the product 4,5-dihydroxy-2,β-dinitrostyrene (14) is recovered at substantially complete purity. This is easily accomplished by washing the solid reaction product mixture, after cooling to room temperature and filtering with, for example, diethyl ether, followed by recrystallization in aqueous ethanol, or preferably by distilling off excess CF₃COOH and recrystallizing from H₂O, using a filter-aid (e.g. Celite, Hy-flo, etc.) to remove the black gum, which is presumably benzyltrifluoroacetate. The obtained product is a bright yellow powder and consists primarily or entirely of the more stable (E) or trans isomer:

$$
\underset{HO}{\overset{HO}{\diagdown}}\diagup\diagdown\underset{NO_2}{\diagup}\overset{H}{\underset{H}{C=C}}\overset{NO_2}{\diagdown} \quad (14\text{-}E)
$$

At this point, rather than proceeding with the conventional three-step chemical reductive cyclization of 4,5-dihydroxy-2,β-dinitrostyrene this compound is directly converted to the object 5,6-dihydroxyindole (7) by catalytic reductive cyclization using hydrogen and a reductive cyclization catalyst in a suitable reaction medium. It was quite surprising to find that the catalytic reductive cyclization would proceed almost quantitatively in view of the fact that when the reaction of (14) (or (14-E)) is carried out in most organic solvents a complex mixture of products is produced from which only very little or none of 5,6-dihydroxyindole (7) can be recovered. However, when, for example, an aqueous reaction medium is used as the reaction medium the conversion from (14) to (7) is quantitative, although the isolated yields of (7) tend to be generally lower, e.g. about 50% or higher, because 5,6-dihydroxyindole is unstable in air. In terms of the starting 3,4-dibenzyloxybenzaldehyde (11) isolated yields of 5,6-dihydroxyindole are in the range of about 35% or higher.

As the suitable reaction medium any medium which is liquid under the reaction conditions and in which cyclization will occur and in which 5,6-dihydroxyindole alone or 5,6-dihydroxyindole and only one or a few minor contaminants is produced or from which pure 5,6-dihydroxyindole can be isolated, can be used.

In particular, polar, hydroxyl group containing solvents such as water, lower alkanols, lower aliphatic carboxylic acids and mixtures thereof are especially suitable as the reaction medium. Examples of the lower alkanols are methanol, ethanol, isopropanol, n-butanol, etc. Examples of the lower aliphatic carboxylic acids are acetic acid, propionic acid, etc. These polar solvents can be used individually or in mixtures of two or more at any proportions in which they are mutually soluble under the reaction conditions.

Generally, percent and rate of conversion to the object 5,6-dihydroxyindole increase as the solvent polarity is increased. When, for example, isopropanol is used as the solvent or as the major solvent component, the 5,6-dihydroxyindole isolated from the solvent requires more purification than when methanol, ethanol, water or acetic acid is used as the solvent or as the major solvent component.

In view of the economy and efficiency of the reaction, the preferred reaction medium is an aqueous reaction medium.

The aqueous reaction medium preferably consists of distilled water. When distilled water alone is used as the reaction medium there is no byproduct formation, i.e. selectivity to 5,6-dihydroxyindole is 100%. A minor amount of a cosolvent such as lower aliphatic carboxylic acid, e.g. acetic acid or ethanol, etc., can be present in the aqueous reaction medium. When the amount of the cosolvent does not exceed about 50%, preferably up to 30%, especially preferably up to about 10% by weight of the total aqueous reaction medium only a single byproduct, which is believed to be 5,6-dihydroxyindoline, is observed. Generally, an amount of cosolvent which is equimolar to the amount of the 4,5-dihydroxy-2,$\beta$-dinitrostyrene (14) can be used.

The catalytic reductive cyclization is performed under a hydrogen atmosphere of, for example, about 40 to 60 psi, preferably about 40 to 55 psi, most preferably about 50 psi. The reaction can proceed at room temperature or slightly elevated temperatures, for example, up to about 50° C.

As the reductive cyclization catalyst a platinum-group metal selected from palladium (Pd), platinum (Pt) or rhodium (Rh) can be used alone or as a mixture. Palladium, alone or with one of the other two metals is preferred. Surprisingly, however, other platinum-group metals, such as ruthenium and iridium whcih are also known as reductive hydrogenation catalysts are not effective in the catalytic reductive cyclization reaction of this invention.

The platinum-group metal catalyst is used in the form supported on a solid carrier. Examples of the solid carrier include carbon, e.g. activated carbon, alumina, silica, diatomaceous earth, silicon carbide, pumice, zeolite, molecular sieve, etc. Carbon and alumina are the preferred solid carriers, and palladium on carbon (Pd/C) which is readily commercially available from a number of sources is especially preferred.

The platinum-group metal supported catalyst can be prepared by any suitable technique. For example, it can be formed by impregnating a solid carrier with an aqueous solution of a water-soluble salt of the platinum-group metal or a mixture of such salts when a mixed platinum-group metal catalyst is used. Examples of the salt of the platinum-group metal include nitrates, sulfates, phosphates, halides, acetates, oxalates, benzoates, chloro complex salts and ammine complex salts of the above-exemplified metals. The impregnated solid carrier is then contacted with an alkali, and the alkali-treated product is then contacted with a reducing agent in the liquid phase (e.g. using such reducing agents as hydrazine, formaldehyde, sodium formate and formic acid) or in the gaseous phase (e.g. using such reducing agents as hydrogen, carbon monoxide and ammonia).

Generally, the amount of supported platinum-group metal can range from about 1 to about 25%, preferably from about 3 to 15%, by weight, based on the weight of carbon. The ratio, by weight, of the catalyst to 4,5-dihydroxy-2,$\beta$-dinitrostyrene can be selected depending on such factors as the amount of supported Pt-group metal, the hydrogen pressure reaction medium, reaction temperature, and the like. Generally, however, in terms of a 10% Pd/C the weight ratio of catalyst to 4,5-dihydroxy-2,$\beta$-dinitrostyrene will range from about 1:0.05 to about 1:100, preferably, from about 1:0.1 to about 1:20. However, at ratios of catalyst:4,5-dihydroxy-2,$\beta$-dinitrostyrene of less than about 1:30, the reaction time can be in excess of about 10 hours, and additional complications may occur. Therefore, the preferred minimum ratio of catalyst to reactant is in the range of about 1:20 to about 1:30. On the other hand, there is no problem when the catalyst is present in great excess so long as the reaction is not run long enough to allow overreduction to 5,6-dihydroxyindoline (e.g. more than about 30 to 60 minutes). Of course, too great an amount of catalyst is generally economically impractical. Therefore, the most preferred weight ratio of catalyst to reactant is in the range of from about 1:0.1 to about 1:30, especially preferably from about 1:0.5 to 1:20, again in terms of a 10% Pd/C catalyst. Within these ratios it will be understood that, at least at the beginning of the reaction, the starting material 4,5-dihydroxy-2,$\beta$-dinitrostyrene should be soluble in the reaction medium.

At the completion of the reaction, which will generally require from about 30 minutes to about 3 hours, preferably from about 45 minutes to about 2 hours, the reaction system may be acidified to a pH of about 5 or less, preferably about 4.5, by the addition of acetic acid. The reaction mixture is then extracted, preferably after filtration, with ether or dichloromethane one or more times, under a nitrogen gas atmosphere, to recover the product 5,6-dihydroxyindole. According to a particular feature of the invention, the isolated yield of 5,6-dihydroxyindole can be further increased by carrying out the isolation of the product 5,6-dihydroxyindole by adding to the acetic acid mixture a compound which will protect the hydroxy groups to give the product compound in a form which is more stable in air. For example, addition of acetic anhydride to the filtered mixture gives 5,6-diacetoxyindole on heating. It is also possible to form the borate ester

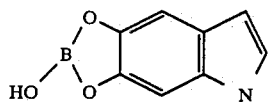

by addition of boric acid to the acetic acid reaction mixture. Generally, any protecting group which is stable to acetic acid can be added to the filtered reaction mixture to give the protected 5,6-dihydroxyindole.

As a still further alternative, the filtered mixture may be used directly for hair dyeing, melanin formation, or other reactions in which 5,6-dihydroxyindole is used in an aqueous medium.

In an alternative embodiment, the 4,5-dihydroxy-2,$\beta$-dinitrostyrene reactant can be prepared by reaction of 4,5-dihydroxy-2-nitrobenzaldehyde with $CH_3NO_2$ under substantially the same conditions as shown by Beer, et al (see Scheme I) to produce a mixture of (Z)-4,5-dihydroxy-2,$\beta$-dinitrostyrene (2) with 1-(4',5'-dihydroxy-2'-nitrophenyl)-2-nitroethanol (3) and/or (4). The (Z) (or cis) isomer can be separated from the product mixture by column chromatography (dry silica gel) with 2:1 hexanes:dichloromethane or other suitable eluents. Alternatively, the mixture of (2) and (3) and/or (4) containing the (Z)-isomer can be converted into the more stable (E)-isomer by recrystallization of the mixture from aqueous ethanol.

It is a particular feature of this invention that in the preparation of 4,5-dihydroxy-2-nitrobenzaldehyde (1) the conversion of 6-nitropiperonal (9) to 5-chloromethoxy-4-hydroxy-2-nitrobenzaldehyde (10) from which the chloromethoxy group is cleaved to produce (1), is produced in high yields, regardless of the amount of the starting material.

According to this feature of the invention, 6-nitropiperonal is converted to (10) by cleavage of the methylenedioxy group using $AlCl_3$ which has an affinity for ether oxygens. The use of the $AlCl_3$-dichloroethane ($ClCH_2CH_2Cl$) system for cleavage of methylenedioxy ether is shown by Avery, et al. However, according to Avery, et al high temperature (25° C.) and long reaction time (2 hours) are used, and under these excessive conditions the yields of (10) are reduced, especially at amounts of the starting material in excess of about 1 gram.

According to this invention, the yields of (10) are maximized by maintaining the reaction temperature at 10° C. or less, especially from −5° C. to 10° C., for a reaction time of about 75 minutes or less, especially from about 40 to 75 minutes. Thus, according to experiments by the inventor when the procedure of Avery, et al [KI, THF, 6N HCl, reflux] are reproduced for more than 1 gram of starting material, the yields of product become unacceptable, i.e. on a scale of 1 to 5 grams, an oil, from which 50 to 60% of pure 4,5-dihydroxy-2-nitrobenzaldehyde (1) is isolated, results, and the yield falls to approximately 20% as the amount of starting material is increased to about 25 grams.

In the methylenedioxy cleavage, any dichloro(lower-)alkane can be used as the solvent, especially dichloromethane and dichloroethane, especially preferably dichloroethane. The yields of 5-chloromethoxy-4-hydroxy-2-nitrobenzaldehyde (10) using $AlCl_3$-$ClCH_2CH_2Cl$ under the above specified reaction conditions typically range from 93 to 97%, after recrystallization, regardless of the amount of starting material.

Standard ether cleavage procedures convert (10) to (1). Presumably, electron withdrawal by the chlorine of the chloromethyl group and the p-$NO_2$ group makes ether cleavage particularly easy. Cleavage with either 6N HCl or 48% HBr, under mild conditions, gives (1) in high yield (80-100%). HBr cleavage is faster, and there is less byproduct formation. Stirring (10) with 48% HBr, at ambient temperature (2320 C.), affords (1) in 100% yield. The formation of (1) starting from piperonal (8) is shown in the following Scheme III.

SCHEME III

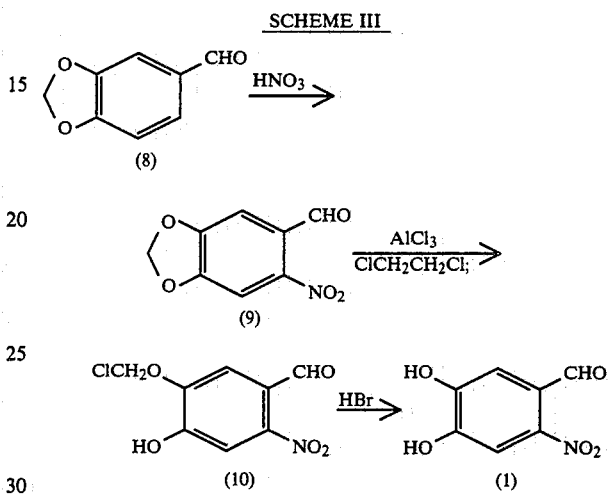

The chloromethyl group may also be removed with pyridine—$AlCl_3$, although in lower yield. Dry pyridine is added to a cooled (0° C.) mixture of (10), $AlCl_3$ and methylene chloride in a 1:1.1:4.4 molar ratio. When addition is complete, the reaction is warmed to 47° C. for 18 hours. After acidification with dilute HCl, 4,5-dihydroxy-2-nitrobenzaldehyde is extracted from the reaction mixture with ether. Dechloromethylation is not a high yield process without isolation of (10), i.e. addition of pyridine or $AlCl_3$ and pyridine to the $AlCl_3$—dichloroethane mixture used to open the methylenedioxy ring does not effect dechloromethylation to an acceptable degree under these conditions.

The invention will now be illustrated by way of the following examples in which all parts and percentages are on a weight basis, unless otherwise indicated.

In the following examples, melting points were taken on a Thomas-Hoover capillary melting point apparatus, and are uncorrected. $^1$NHMR spectra were obtained on a Perkin-Elmer R12B NMR spectrometer, with tetramethylsilane as the internal standard. Mass spectra were obtained on a Finnigan 4000/GC/MS/DS System. IR spectra were taken on a Perkin-Elmer 137 infrared spectrophotometer. Microanalyses were done by Micro-Analysis, P.O. Box 5800, Wilmington, Del.

EXAMPLE 1

3,4-Dibenzyloxy-$\beta$-nitrostyrene (12)

A mixture of 79.5 g (1.25 mol) of 3,4-dibenzyloxybenzaldehyde (11) (available from Aldrich Chemical Co.), 47 g $CH_3CO_2NH_4$, 47 g $CH_3NO_2$, and 400 ml $CH_3CO_2H$ is refluxed for two hours. The mixture is cooled to 23° C. to precipitate the product. The yellow solid is isolated by filtration, washed with ethanol, and air dried. Recrystallization from $CH_3CO_2H$—$C_2H_5OH$ gives 67.2 g (74.5%) of (12): mp 118°–119° C.

EXAMPLE 2

(E)-4,5-Dibenzyloxy-2,β-dinitrostyrene (13)

3,4-Dibenzyloxy-β-nitrostyrene (12) (67.2 g; 0.186 mol) is dispersed in 1.5 L $CH_3CO_2H$. $HNO_3$(d 1.42) is added until the temperature reaches 40° C. The mixture is cooled to 20° C., and the remainder of the 375 mL $HNO_3$ is added without further cooling. After stirring at 23° C. for three hours, the reaction mixture is poured onto 2 kg of ice, and filtered. The yellow powder is washed well with $H_2O$. Recrystallization from $CH_3CO_2H$ affords 70.3 g (93%) of (13) as yellow needles; mp 162°–164° C.

EXAMPLE 3

(E)-4,5-dihydroxy-2-β-dinitrostyrene (14-E)

A mixture of 72 g (0.177 mol) of 4,5-dibenzyloxy-2,β-dinitrostyrene (13) is refluxed in 500 ml trifluoroacetic acid ($CF_3CO_2H$), under $N_2$, for three hours. The cooled reaction mixture is filtered, and the solid is washed with diethyl ether. An insoluble brown solid remains. The ether is removed at reduced pressure, and the solid is recrystallized from aqueous ethanol, yielding 40 g of a bright yellow powder, the majority of which is identified as (14-E): mp 169°–170° C.; mass spectrum, m/e 226 (M+), 180, 165, 150, 134, 124, 110, 97, 88, 76, 68; $^1$HNMR ($d_6$-$Me_2CO$) δ8.47(d, J=13.2 Hz,1H), δ7.9(d,J=13.2 Hz,1H), δ7.62(s,1H), 7.19(s,1H).

Alternatively, after the reaction is complete, excess $CF_3CO_2H$ is removed by distillation and the solid is recrystallized from $H_2O$ using a filter-aid, such as Celite or Hy-flo, to remove the brown, gummy solid which is a byproduct of the reaction.

EXAMPLE 4

5,6-Dihydroxyindole (7)

(E)-4,5-Dihydroxy-2,β-dinitrostyrene (14) (1 g; 0.00044 mol) is dispersed in 50 ml distilled $H_2O$ in a Parr bottle, and 0.1 g 10% Pd/C is added. The reaction mixture is shaken on a Parr hydrogenator at 50 psi $H_2$ for 45 minutes. $CH_3CO_2H$ is added to bring the pH to 4.5, and the reaction mixture is extracted with 4×50 ml diethyl ether or dichloromethane, in a nitrogen atmosphere. The combined ether extracts are dried over $Na_2SO_4$, then filtered. The ether is removed at reduced pressure, without heating. 5,6-Dihydroxyindole is obtained in 50% yield (0.33 g): mp 140° C. (dec).

When Pd on alumina, Pt on carbon, Pt on alumina, Rh on carbon or Rh on alumina is used as the catalyst in place of the Pd/C catalyst similar results are obtained. Similarly, methanol, ethanol, isopropanol, acetic acid or mixtures thereof can be used to replace part or all of the distilled water without adversely affecting the results. However, when ruthenium, either in the form of ruthenium on powdered carbon or as $RuCl_2$-$(CO_2)(Ph_3P)_2$(13.4% Ru) is used in place of the 10% Pd/C catalyst, little or no 5,6-dihydroxyindole is produced in 2 to 3 hours.

EXAMPLE 5

5-Chloromethoxy-4-hydroxy-2-nitrobenzaldehyde (10)

$AlCl_3$ (6 g) and dry dichloroethane (15 ml) are added to a three-neck round bottom flask, which has been purged with $N_2$, and the dispersion is cooled to −5°. A solution of 6-nitropiperonal (3 g; 0.0154 mol) (available from Aldrich Chemical Co.) in 12 ml dry dichloroethane is added to the dispersion, in one portion, while the temperature and $N_2$ atmosphere are maintained. The reaction mixture is stirred for 1.25 hours, and 100 ml $H_2O$ (0°) is added. The emulsion is stirred for 15 minutes, then extracted with 3×100 ml ethyl acetate. The combined organics are washed with saturated NaCl, then dried over $Na_2SO_4$. After filtration, the ethyl acetate is removed at reduced pressure. Recrystallization from ethyl acetate gives 3.45 g (97%) of (10): mp 160°–161° C.

EXAMPLE 6

4,5-Dihydroxy-2-nitrobenzaldehyde (1)

5-Chloromethoxy-4-hydroxy-2-nitrobenzaldehyde (10) (3 g; 0.013 mol) is stirred at 23° C. with 15 ml 48% HBr for two days. The precipitate is removed by filtration, and washed well with $H_2O$, giving 2.2 g (93%) of 4,5-dihydroxy-2-nitrobenzaldehyde (1). The remainder of the product is isolated by ether extraction of the filtrate. Drying the combined ether extracts over $Na_2SO_4$, filtering, and removing the ether at reduced pressure, gives the remaining 0.17 g (7%) of (1): mp 201°–203° C.; mass spectrum, m/e 183 (M+); $^1$HNMR ($d_6$-$Me_2CO$) δ10.59 (br s,2H), δ10.2(s,1H), δ7.6(s,1H), δ7.3(s,1H).

EXAMPLE 7

4,5-Dihydroxy-2-nitrobenzaldehyde (1)

To a stirred, cooled (0° C.) dispersion of 1.52 g (0.00658 mol) of 5-chloromethoxy-4-hydroxy-2-nitrobenzaldehyde (10), 1 g $AlCl_3$, and 10 ml dry dichloroethane, 2.4 ml of dry pyridine are added. During addition, the reaction mixture is protected from atmospheric moisture, and the temperature is kept below 35° C. When addition is complete, the temperature is raised to 47° C., and maintained for 18 hours. 6N HCl is added, keeping the temperature at 30°–35° C., until the mixture is acidic to Congo Red indicator paper. The acidic solution is extracted with diethyl ether, and the combined ether extracts are dried over $Na_2SO_4$. After filtration, the ether is removed at reduced pressure, giving 0.82 g (68%) of (1): mp 201°–202°° C.

EXAMPLE 8

(Z)-4,5-dihydroxy-2,β-dinitrostyrene (2)

A solution of 1.61 g KOH, 2.3 ml $H_2O$ and 23 ml 95% $C_2H_5OH$ is added dropwise to a mixture of 2.3 g (0.0126 mol) of 4,5-dihydroxy-2-nitrobenzaldehyde (1), 1.4 g $CH_3NO_2$, and 23 ml 95% $C_2H_5OH$ at 0° C. The dispersion is stirred at 0° C. for 30 hours, then poured into 50 g $H_2O$ (0° C.) and acidified with cold (0° C.) 6N HCl. The mixture is extracted with 3×100 ml cold (015° C.) diethyl ether, and the combined ether extracts are washed with cold (0° C.) $NaHSO_3$. The organics are dried over $Na_2SO_4$. After filtration, the ether is removed at reduced pressure, without heating. The light yellow powder (2.97 g) is a 1:1 mixture of 1-(4',5'-dihydroxy-2'-nitrophenyl)-2-nitroethanol and (Z)-4,5-dihydroxy-2,β-dinitrostyrene (2). It is uncertain which of the enantiomeric alcohols, (3) or (4), is present, or whether the product contains a mixture of both. (Z)-4,5-dihydroxy-2,β-dinitrostyrene (2) is separated from the product mixture by column chromatography (dry silica gel) with 2:1 hexanes:dichloromethane: mp 158° C.; mass spectrum, m/e 226 (M+); $^1$HNMR ($d_6$-$Me_2CO$) δ7.62 (s, 1H), δ7.19(s,1H), δ5.95(d,J-4 Hz,1H), δ5.81 (d,J-4 Hz,1H).

After chromatography, 1.48 g (49%) of the alcohol fraction (3 and/or 4) are isolated: mp 147°–149° C.; mass spectrum, m/e 244 (M+), 226, 227, 180, 153, 136, 123, 108, 97, 88, 79, 69; $^1$HMNR (d$_6$-DMSO) $\delta$7.62(s,1H), $\delta$7.19(s,1H), $\delta$4.66(m,3H), $\delta$4.2(s,1H); Anal. Calcd. for $C_8H_8N_2O_7$: C, 39.34; H, 3.28; N, 11.48; O, 45.90. Found: C, 39.32; H, 3,67; N, 11.43; O, 45.77.

EXAMPLE 9

(E)-4,5-dihydroxy-2,$\beta$-dinitrostyrene (14-E)

The mixture of products containing (2) and (3) and/or (4) obtained from Example 8 is transformed into (14-E) by warming 2 g of the mixture with 0.5 g CH$_3$CO$_2$Na and 15 ml (CH$_3$CO)$_2$O at 70° C. for one hour. The mixture is poured onto 50 g of ice and stirred for one hour. The dispersion is filtered, and the solid is washed well with H$_2$O. The solid thus obtained is refluxed in 50 ml 95% ethanol for two hours. Removing the solvent at reduced pressure affords a bright yellow solid, which is identical to the sample prepared in Example 3: mp 169°–170° C.

What is claimed is:

1. A method for preparing 5,6-dihydroxyindole in high yield and purity which comprises subjecting 4,5-dihydroxy-2,$\beta$-dinitrostyrene to catalytic reductive cyclization with hydrogen in the presence of a platinum group metal catalyst which is palladium, platinum, rhodium or a mixture thereof in a polar hydroxylic solvent to produce 5,6-dihydroxyindole.

2. The method of claim 1 wherein the platinum group metal is supported on a solid carrier.

3. The method of claim 1 wherein the catalyst comprises palladium, platinum or rhodium supported on a solid carbon or alumnina catalyst support.

4. The method of claim 1 wherein the catalyst comprises palladium on carbon.

5. The method of claim 1 wherein the liquid reaction medium is selected from the group consisting of water, methanol, ethanol, isopropanol, acetic acid and mixtures thereof.

6. The method of claim 1 wherein the liquid reaction medium is an aqueous reaction medium.

7. The method of claim 6 wherein the aqueous reaction medium consists essentially of distilled water.

8. The method of claim 6 wherein the aqueous system consists essentially of a major amount of water and a minor amount of acetic acid.

* * * * *